United States Patent [19]

Sollman

[11] 4,255,582
[45] Mar. 10, 1981

[54] (−)-α-{2-[BIS(1-METHYLETHYL)AMINO]E-THYL}-α-PHENYL-2-PYRIDINEACETA-MIDE AND PHARMACOLOGICALLY ACCEPTABLE SALTS THEREOF

[75] Inventor: Paul B. Sollman, Wilmette, Ill.

[73] Assignee: G. D. Searle & Co., Skokie, Ill.

[21] Appl. No.: 8,892

[22] Filed: Feb. 2, 1979

[51] Int. Cl.³ .......................................... C07D 213/56
[52] U.S. Cl. .................................... 546/323; 424/266
[58] Field of Search ........................................ 546/323

[56] References Cited

U.S. PATENT DOCUMENTS

| | | | |
|---|---|---|---|
| 3,225,054 | 12/1965 | Cusic et al. | 546/323 |
| 3,985,370 | 10/1976 | Cusic et al. | 260/239 D |

OTHER PUBLICATIONS

Circulation, Part II, vol. 58, No. 4, Abstract Nos. 712–715 (pub. by American Heart Assn., Inc.), Oct. 1978.

*Primary Examiner*—Alan L. Rotman
*Attorney, Agent, or Firm*—John M. Brown; James R. Henes

[57] ABSTRACT

Preparation of antiarrhythmic (−)-α-{2-[bis(1-methylethyl)amino]ethyl}-α-phenyl-2-pyridineacetamide and pharmacologically acceptable salts thereof characterized by advantageously diminished and/or favorably altered side-effects such as anticholinergic activity is disclosed.

3 Claims, No Drawings

(−)-α-{2-[BIS(1-METHYLETHYL)AMINO]ETHYL}-α-PHENYL-2-PYRIDINEACETAMIDE AND PHARMACOLOGICALLY ACCEPTABLE SALTS THEREOF

This invention relates to (−)-α-{2-[bis(1-methylethyl)amino]ethyl}-α-phenyl-2-pyridineacetamide, pharmacologically acceptable salts thereof, and processes whereby these substances can be prepared. More particularly, this invention provides the levorotatory base having the formula

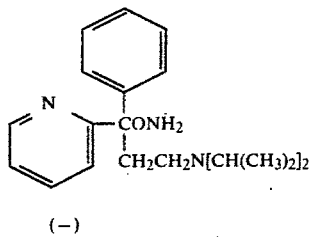

(−)

and salts thereof with acids of the formula

HT wherein T represents 1 equivalent of an anion such as chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like which, in combination with the cationic portion of a salt aforesaid, is neither therapeutically nor otherwise incompatible.

The substances to which this invention relates are useful because of their valuable pharmacological properties. Thus, for example, they are antiarrhythmic agents unpredictably distinguished from (±)-α-{2-[bis(1-methylethyl)-amino]ethyl}-α-phenyl-2-pyridineacetamide, (+)-α-{2-[bis(1-methylethyl)amino]ethyl}-α-phenyl-2-pyridineacetamide, and salts, thereof by their advantageously diminished and/or favorably altered anticholinergic side-effect.

Antiarrhythmic utility can be demonstrated via a standardized test for the capacity of a substance to counteract the ventricular ectopic arrhythmia induced by a two-stage ligation of the anterior descending branch of the left coronary artery in the intact dog, substantially as described in U.S. Pat. No. 3,985,370. The phosphoric acid salt of (−)-α-{2-[bis(1-methylethyl)amino]ethyl}-α-phenyl-2-pyridineacetamide, the enantiomer thereof, and the racemic mixture of these two enantiomers (disopyramide phosphate) produced essentially equivalent antiarrhythmic responses in this test.

The comparative anticholinergic activity of two substances can be demonstrated via the cumulative dose-response curve technique described by J. M. Van Rossum in Arch. intern. Pharmacodynamie, 143, 299 (1963) employing segments of guinea pig ilea mounted in tissue baths as described by J. H. Sanner in Arch. intern. Pharmacodynamie, 180, 46 (1969). This technique provides means of evaluating both the mechanism and the degree of acetylcholine antagonism induced. Preliminarily, concentrations of the substances sufficiently varied to fully characterize the antagonism are determined, 3, 6, 12, and 24 μg/ml being appropriate when the phosphoric acid salt of (−)-α-{2-[bis(1-methylethyl)amino]ethyl}-α-phenyl-2-pyridineacetamide and the enantiomer thereof are the substances involved. Cumulative control dose-response curves are established for paired tissue baths containing ileal segments from the same animal by adding acetylcholine in increments such that the concentration thereof in each bath is increased by 0.5 log unit each time. Cumulative dose-response curves are likewise established in the presence of each of the predetermined characterizing concentrations of one of the substances in one of the baths and—concurrently at the same concentration—the second substance in the other, there being a 15-min. equilibration period preceeding the initial addition of incremental acetycholine in each instance and fresh ileal segments being employed whenever the substance concentrations are changed. In implementing the foregoing technique, a sequence of four pairs of cumulative dose-response curves in each of the two baths are used to characterize the effect of each of the four concentrations of the substances in either bath. A total of twelve such sequences employing ileal segments from twelve different animals are employed in a design such that (1) the sequence of the four concentrations is randomized independently on each occasion and (2) each substance is alloted randomly six times to each bath. The anticholinergic response to the phosphoric acid salt of (−)-α-{2-[bis(1-methylethyl)amino]ethyl}-α-phenyl-2-pyridineacetamide vis-a-vis the response to the enantiomer thereof was advantageously diminished and/or favorably altered when evaluated via the foregoing procedure.

For therapeutic purposes, the substances of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences", 14 Ed., Merck Publishing Company, Eaton, Pa., 1965.

Appropriate dosages, in any given instance, of course depend upon the nature and severity of the condition treated, the route of administration, and the species of mammal involved, including its size and any individual idiosyncrasies which obtain. In general, and insofar as consistent with the foregoing considerations, daily doses, incrementally administered, of from 2 to 50 mg/kg per os or 9–16 mg/kg intravenously are suggested. Illustrative of such dosage is 5 mg/kg of (−)-α-{2-[bis(1-methylethyl)amino]ethyl}-α-phenyl-2-pyridineacetamide q.i.d. per os or 2 mg/kg thereof during 5 min., followed by 0.4 mg/kg/hr. for ≦18 hr. intravenously. An alternative intravenous dosage consists of 1 mg/kg/hr. for 3 hr. and 0.4 mg/kg/hr. thereafter for ≦18 hr., plus 0.5 mg/kg/hr. during the first 5 min., repeated at 5-min. intervals if appropriate monitoring warrants. Illustrative dosages of pharamaceutically acceptable acid addition salts of (−)-α-{2-[bis(1-methylethyl)amino]ethyl}-α-phenyl-2-pyridineacetamide, such as the phosphoric acid salt of (−)-α-{2-[bis(1-methylethyl)amino]ethyl}-α-phenyl-2-pyridineacetamide, are commonly increased in proportion to the greater molecular weight of the involved salt as compared to that of the base. Those skilled in the art will of course recognize that dosage must always be adjusted in accordance with the response of the patient.

Preparation of the substances of this invention proceeds by contacting (±)-α-{2-[bis(1-methylethyl)amino]-ethyl}-α-phenyl-2-pyridineacetamide (U.S. Pat. No. 3,225,054) with (±)-tartaric acid in a mixture of absolute ethanol with 1,1′-oxybisethane such that the (+)-tartaric acid salt of (−)-α-{2-[bis(1-methylethyl)amino]ethyl}-α-phenyl-2-pyridineacetamide crystallizes out, whereupon it is purified by recrystallization from absolute ethanol until the specific rotation of a 5% solution of said salt in methanol at room temperature, referred to the D line of sodium, is approximately +35.6°. Contacting this salt, thus purified, with concentrated ammonium hydroxide in an appropriate mixture of water and hexane affords crystalline (−)-α-{2-[bis(1-methylethyl)amino]ethyl}-α-phenyl-2-pyridineacetamide, which is converted to the aforesaid or another salt of the invention by simple admixture—preferably but not invariably in a solvent medium—with any of various inorganic and strong organic acids, the anionic portion of which conforms to T as hereinabove defined.

The following examples describe in detail preparations illustrative of the present invention and means which have been devised therefor. However, the invention is not to be construed as limited thereby, either in spirit or in scope, since it will be apparent to those skilled in the art that many modifications, both of techniques and of materials, may be practiced without departing from the purpose and intent of this disclosure. Throughout the examples hereinafter set forth, temperatures are given in degrees centigrade and relative amounts of materials in parts by weight, except as otherwise noted. As indicated above, specific rotations connote determinations made in 5% methanol solutions at room temperature, referred to the D line of sodium.

EXAMPLE 1

Preparation of the (+)-tartaric acid salt of (−)-α-{2-[bis(1-methylethyl)amino]ethyl}-α-phenyl-2-pyridineacetamide To a solution of 165 parts of (±)-α-{2-[bis(1-methylethyl)amino]ethyl}-α-phenyl-2-pyridineacetamide and 35 parts of (+)-tartaric acid in 200 parts of absolute ethanol is added 190 parts of anhydrous 1,1′-oxybisethane. The crystalline precipitate which forms is filtered off and recrystallized from absolute ethanol until $[\alpha]_D = +35.6°$. The substance thus prepared and characterized is the (+)-tartaric acid salt of (−)-α-{2-[bis(1-methylethyl)amino]ethyl}-α-phenyl-2-pyridineacetamide.

EXAMPLE 2

Preparation of (−)-α-{2-[bis(1-methylethyl)amino]-ethyl}-α-phenyl-2-pyridineacetamide A solution of 88 parts of the (+)-tartaric acid salt of (−)-α-{2-[bis(1-methylethyl)-amino]ethyl}-α-phenyl-2-pyridineacetamide in 400 parts of water is stirred with 265 parts of hexane while 72 parts of 28% ammonium hydroxide is introduced. The crystalline precipitate which forms is filtered off and recrystallized from hexane. The substance thus isolated is (−)-α-{2-[bis(1-methylethyl)amino]ethyl}-α-phenyl-2-pyridineacetamide, $[\alpha]_D - 19°$.

EXAMPLE 3

Preparation of the phosphoric acid salt of (−)-α-{2-[bis(1-methylethyl)amino]ethyl}-α-phenyl-2-pyridineacetamide To a solution of 214 parts of (−)-α-{2-[bis(1-methylethyl)amino]ethyl}-α-phenyl-2-pyridineacetamide in 790 parts of absolute ethanol is added a solution of 73 parts of 85% phosphoric acid in 160 parts of absolute ethanol. The crystalline precipitate which forms is filtered off and dried in air. The substance thus isolated is the phosphoric acid salt of (−)-α-{2-[bis(1-methylethyl)amino}-α-phenyl-2-pyridineacetamide, $[\alpha]_D + 28.2$.

EXAMPLE 4

Preparation of capsules

A mixture of 1935 parts of the phosphoric acid salt of (−)-α-{2-[bis(1-methylethyl)-amino]ethyl}-α-phenyl-2-pyridineacetamide, 1170 parts of corn starch, and 1170 parts of lactose is sifted through a 40-mesh screen, then mixed with 225 parts of talc. The resultant mixture is filled into no. 1 and no. 3 hard gelatin capsules individually containing 193.5 and 64.5 mg of the salt, respectively.

EXAMPLE 5

Preparation of tablets

A mixture of 1935 parts of the phosphoric acid salt of (−)-α-[2-[bis(1-methylethyl)-amino]ethyl}-α-phenyl-2-pyridineacetamide, 1170 parts of corn starch, and 1170 parts of lactose is sifted through a 40-mesh screen, then granulated with water. The granulated material is—consecutively—tray-dried at 60° for 8 hr., comminuted, sifted through a 12-mesh screen, and mixed with 225 parts of talc. The resultant mixture is compressed into 450-mg tablets.

EXAMPLE 6

Preparation of sterile solutions

A solution of 258 parts of the phosphoric acid salt of (−) -α-{2-[bis(1-methylethyl)amino]ethyl}-α-phenyl-2-pyridineacetamide in 10,000 parts of water is filtered and thereupon filled into 10-ml. ampuls. The ampuls are sealed and then sterilized by heating in saturated steam at 121° for 20 min.

What is claimed is:

1. (−)-α-{2-[Bis(1-methylethyl)amino]ethyl}-α-phenyl-2-pyridineacetamide and pharmacologically acceptable salts thereof.

2. A compound according to claim 1 which is a pharmacologically acceptable salt of (−)-α-{2-[bis(1-methylethyl)amino]ethyl}-α-phenyl-2-pyridineacetamide.

3. A compound according to claim 1 which is the phosphoric acid salt of (−)-α-{2-[bis(1-methylethyl)amino]-ethyl}-α-phenyl-2-pyridineacetamide.

* * * * *